(12) United States Patent
Baradarian et al.

(10) Patent No.: US 10,595,953 B2
(45) Date of Patent: Mar. 24, 2020

(54) ON PATIENT SURGICAL PROCEDURAL INSTRUMENT TRAY

(75) Inventors: Samuel Baradarian, San Diego, CA (US); Stephen Anthony Tunnell, Oceanside, CA (US)

(73) Assignee: Connected Rock, Inc., Carlsbad, CA (US)

( * ) Notice: Subject to any disclaimer, the term of this patent is extended or adjusted under 35 U.S.C. 154(b) by 0 days.

(21) Appl. No.: 13/076,303

(22) Filed: Mar. 30, 2011

(65) Prior Publication Data

US 2011/0290689 A1    Dec. 1, 2011

Related U.S. Application Data

(60) Provisional application No. 61/319,723, filed on Mar. 31, 2010.

(51) Int. Cl.
*A61B 50/33*    (2016.01)
*A61B 46/23*    (2016.01)

(52) U.S. Cl.
CPC .............. *A61B 50/33* (2016.02); *A61B 46/23* (2016.02)

(58) Field of Classification Search
CPC ... A61B 19/0271; A61B 19/10; A61B 19/087; A61B 19/088; A61B 19/38; A61B 2019/0281; A61B 19/02; A61B 46/23; A61B 2050/155; A61B 2019/0251; A61B 50/33; A47B 31/00; B25H 3/028; B25H 3/06; A71G 11/003; A71G 11/006; A47G 11/004; B69F 9/001; A61L 2/07; Y10T 24/1365; Y10T 24/1408; Y10T 24/1406; Y10T 24/13; Y10T 24/14

USPC ......... 220/676, 575, 574; 128/872, 849–856, 128/132 D, 1 R; 206/518, 370; 108/42; 224/413, 904–905, 257, 255

See application file for complete search history.

(56) References Cited

U.S. PATENT DOCUMENTS

| | | | | |
|---|---|---|---|---|
| 956,534 | A | * | 5/1910 | Lahey .................... B42F 9/001 108/43 |
| 1,667,264 | A | * | 4/1928 | Minnick ......................... 223/82 |
| 2,989,634 | A | * | 6/1961 | Allen ................... A61B 6/4283 378/177 |
| 3,565,067 | A | * | 2/1971 | Bayer et al. .................. 128/853 |
| 3,667,458 | A | * | 6/1972 | Krebs ........................... 128/853 |
| 3,770,119 | A | * | 11/1973 | Hultberg et al. ............. 206/439 |
| 3,998,221 | A | * | 12/1976 | Collins ......................... 128/855 |
| 4,042,109 | A | | 8/1977 | Barcan |
| 5,005,590 | A | | 4/1991 | Eldridge |
| 5,170,804 | A | | 12/1992 | Glassman |
| 5,284,099 | A | * | 2/1994 | Cohen ............................ 108/90 |

(Continued)

OTHER PUBLICATIONS

U.S. Appl. No. 13/107,662, filed May 13, 2011, 2011-0298631.

(Continued)

*Primary Examiner* — Anthony D Stashick
*Assistant Examiner* — James M Van Buskirk
(74) *Attorney, Agent, or Firm* — Troutman Sanders LLP

(57) ABSTRACT

An instrument tray is configured for use with surgical and/or other invasive or non-invasive medical procedures, such as in operating rooms or ICU rooms within a hospital, for example. The tray facilitates a safe transfer of instruments between a procedural team and performing the procedure. In an embodiment the surgical tray may be attached directly to the patient and/or patient's drapes so that the tray may rest upon the patient.

9 Claims, 4 Drawing Sheets

(56) References Cited

U.S. PATENT DOCUMENTS

| | | | | |
|---|---|---|---|---|
| D347,733 S | * | 6/1994 | Miller | D3/226 |
| D451,347 S | * | 12/2001 | Kleckauskas | D7/359 |
| D472,767 S | * | 4/2003 | Gebhardt | D7/545 |
| 7,104,201 B2 | * | 9/2006 | Comeaux et al. | 108/90 |
| D575,989 S | * | 9/2008 | McFarland | D7/554.3 |
| 7,506,763 B2 | * | 3/2009 | Hatcher | 206/565 |
| 7,810,683 B2 | * | 10/2010 | Chan | 224/222 |
| 2004/0011840 A1 | | 6/2004 | Griesbach et al. | |
| 2007/0215507 A1 | | 9/2007 | Glenn et al. | |
| 2010/0270442 A1 | * | 10/2010 | Zoland | A61B 50/13 |
| | | | | 248/121 |

OTHER PUBLICATIONS

U.S. Appl. No. 61/534,837, filed Sep. 14, 2011.
PCT/US11/36526, May 13, 2011, WO2011/143618.
PCT/US11/30588, Mar. 30, 2011, WO2011/123565.

* cited by examiner

ON PATIENT SURGICAL PROCEDURAL INSTRUMENT TRAY

REFERENCE TO PRIORITY DOCUMENT

This application claims priority of U.S. Provisional Patent Application Ser. No. 61/319,723 filed on Mar. 31, 2010. The disclosure of the Provisional Patent Application is hereby incorporated by reference in its entirety.

BACKGROUND

The present disclosure relates to surgical and procedural devices. More particularly the present disclosure relates to surgical and other invasive medical procedures in operating rooms or Intensive Care Units or Procedural rooms within the hospital today where the safe transfer of instruments between the procedural team and Physician or Surgeon is necessary.

Conventional surgical instrument trays are used to rest and or pass instruments during a surgery or other medical procedure. However, these trays are free standing and are typically located close to bedside or operating table side. This means the instruments and surgical tools are located to the side of the physician. In order for the physician to access the instrument, he or she must turn away from the patient. Some free standing carts have extending arms that permit the physician to move the tray's surface closer. However, these carts undesirably consume foot space, as well as table or bedside space. Additionally these free standing trays are cumbersome to move.

In order to get around the deficiencies associated with trays, patient drapes have been developed with impregnated magnets to hold the instruments and tools for ready access. Unfortunately, these drapes do not provide a support plane or other surface for the instruments to rest upon. Additionally, because instruments and tools often include multiple configurations (including different weights and metal compositions) the magnetic force is often insufficient to hold the weight of the instrument. This results in the instrument accidentally falling or otherwise detaching from the drape.

In many cases, during procedures or in the operating room it is necessary to adjust the patient's position. As an example, in the case of a thoracotomy procedure the patient may be positioned in various side positions and as the surgeon requests that the patient be moved or repositioned, all the trays must be moved and replaced before the surgery or procedure can continue. Today, patients in preparation for their surgery or procedure are draped in paper or plastic sheets to create a barrier of protection and isolate the area of the operation or procedure from the remaining patient's anatomy. This can be cumbersome.

SUMMARY

In view of the foregoing, there is a need for improved systems for accessing and handling medical instruments, such as surgical instruments.

In one aspect, there is disclosed a surgical tray, comprising: a planar member having an upper surface and a lower surface, wherein the upper surface is configured to support at least one medical instrument; a first drape member extending outwardly from a first side of the planar member; and a second drape member extending outwardly from a second side of the planar member; wherein the surgical tray is configured to be positioned at least partially on a patient.

Other features and advantages should be apparent from the following description of various embodiments, which illustrate, by way of example, the principles of the invention.

DETAILED DESCRIPTION

Before the present subject matter is further described, it is to be understood that this subject matter described herein is not limited to the particular embodiments described, as such may of course vary. It is also to be understood that the language used herein is for the purpose of describing particular embodiments only, and is not intended to be limiting. Unless defined otherwise, all technical terms used herein have the same meaning as commonly understood by one skilled in the art to which this subject matter belongs.

As will be apparent to those of skill in the art upon reading this disclosure, each of the individual embodiments described and illustrated herein has discrete components and features which may be readily separated from or combined with the features of any of the other several embodiments without departing from the scope of the subject described herein. Any recited method can be carried out in the order of events recited or in any other order which is logically possible.

Disclosed is an instrument tray (sometimes referred to as an on-patient tray) that is configured for use with surgical and/or other invasive or non-invasive medical procedures, such as in operating rooms or ICU rooms within a hospital, for example. The tray facilitates a safe transfer of instruments between a procedural team and performing the procedure. In an embodiment a surgical tray is attached directly to the patient and/or patient's drapes so that the tray may rest upon the patient.

Figure 1:
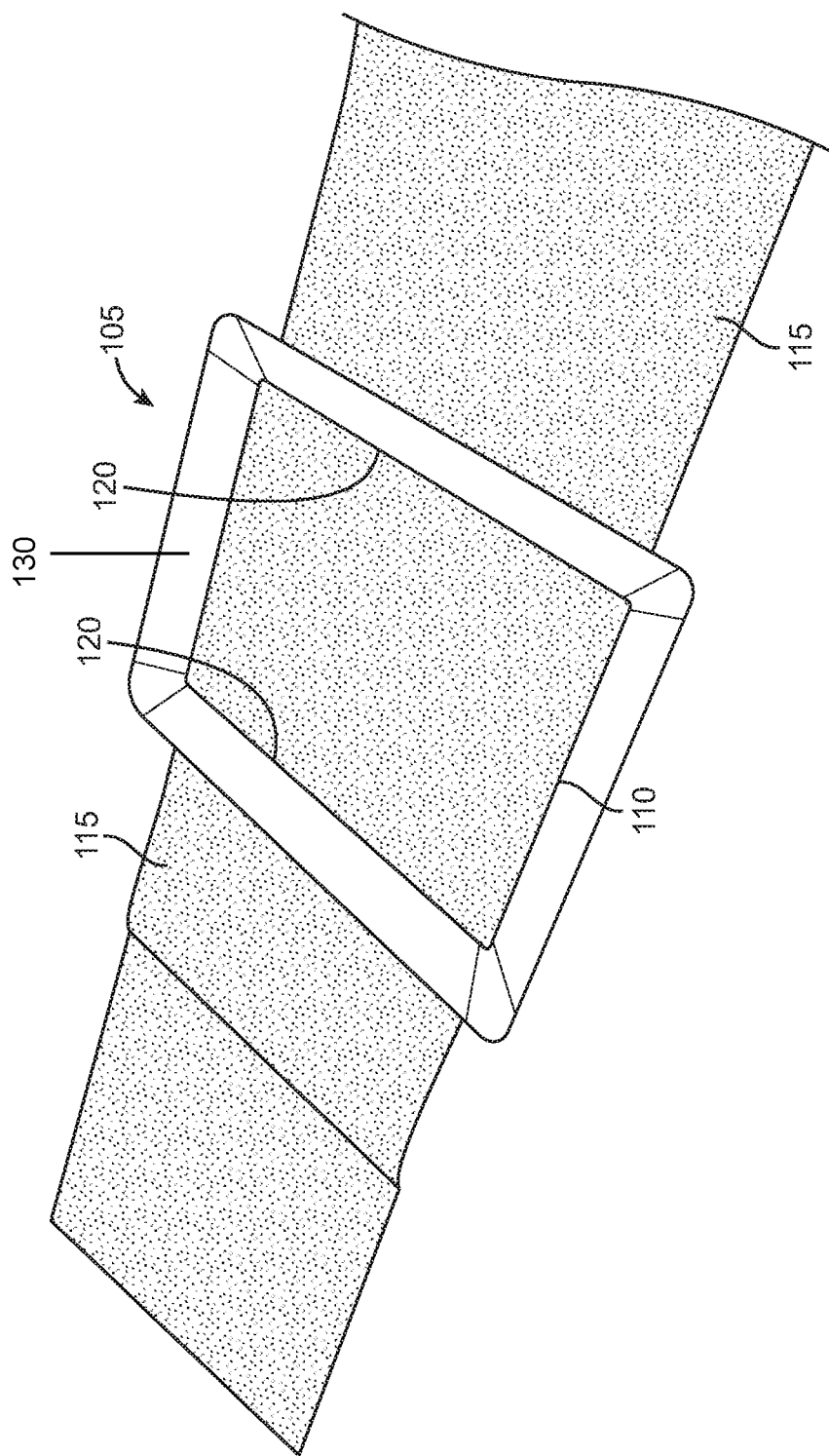
FIG. 1 shows a top view of a first embodiment of a surgical tray.
Figure 2:
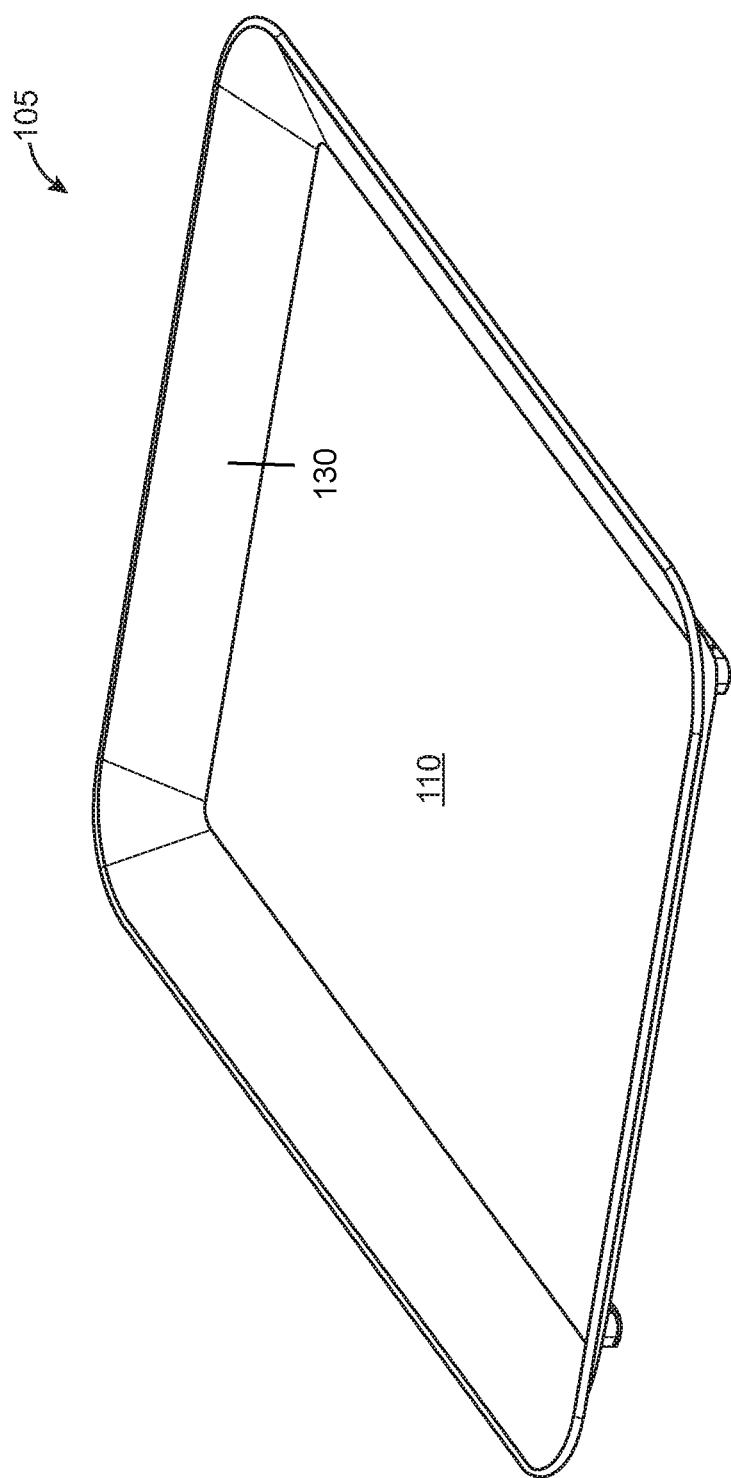
FIG. 2 shows a top view of another surgical tray.

With reference to FIG. 1, a tray 105 includes a generally flat surface 110 that is configured to serve as a support surface for one or more instruments. The surface 110 can be flat or contoured and/or it may include any of a number of features, such as protrusions, slots, seats, etc. for interfacing with the instrument(s). The illustrated embodiment of the tray 105 includes a sloped periphery 130 that serves as a parapet or wall for assisting in retaining the instruments on the surface 110. The sloped periphery 130 may also be a wall or protrusion or any type of feature that is configured to retain the instruments on the surface 110. The surface 110 may be smooth or textured so as to allow the instruments to be picked up easier and prevent instruments from sliding off the tray.

In the illustrated embodiment, the tray 105 is generally rectangular although it should be appreciated that the tray could have any of a variety of shapes and sizes.

The tray 105 is generally configured to be positioned on or in the vicinity of a patient. In an embodiment, the tray 105 is configured to be positioned on top of or partially on top of a patient, such as on the torso of the patient. In this regard, the tray 105 is sufficiently light so as to not provide discomfort to the patient. Moreover, a bottom surface of the tray may be contoured to provide comfort to the patient when positioned atop the patient.

With reference still to FIG. 1, a drape 115 is coupled to the tray 105. The drape 105 can be formed of any suitable piece of fabric, paper, textile, plastic, rubber, or any other suitable material, or combination thereof In an embodiment, the tray 105 has one or more slots 120 that are configured to receive the drape 105 therethrough such that the drape 105 removably or fixedly attaches to the tray 105. The slots 120 serve as means for securing the drape 115 to the tray 105. In this regard, the drape 115 can be positioned through the slot(s) 120 such that the slots retain the drape 115 to the tray 105. The slots 120 are sized such that the drape 115 can slide through the slots 120. In this manner, the drape 115 serves as a contiguous single sheet which forms the tray drapes and the tray base surface, which ends are attached to the patient's surgical drapes using surgical clamps or surgical clips or any other means, including adhesive. The drape 115 can be positioned on top of or beneath the surface 110. In the embodiment shown in FIG. 1, the slots are formed in the outer wall of the sloped periphery 130 of the tray 105. This positions the slots above the top surface 110 of the tray 105. Thus, when the drape is positioned through the slots, the drape is positioned adjacent the top surface 110 of the tray 105.

Figure 3:
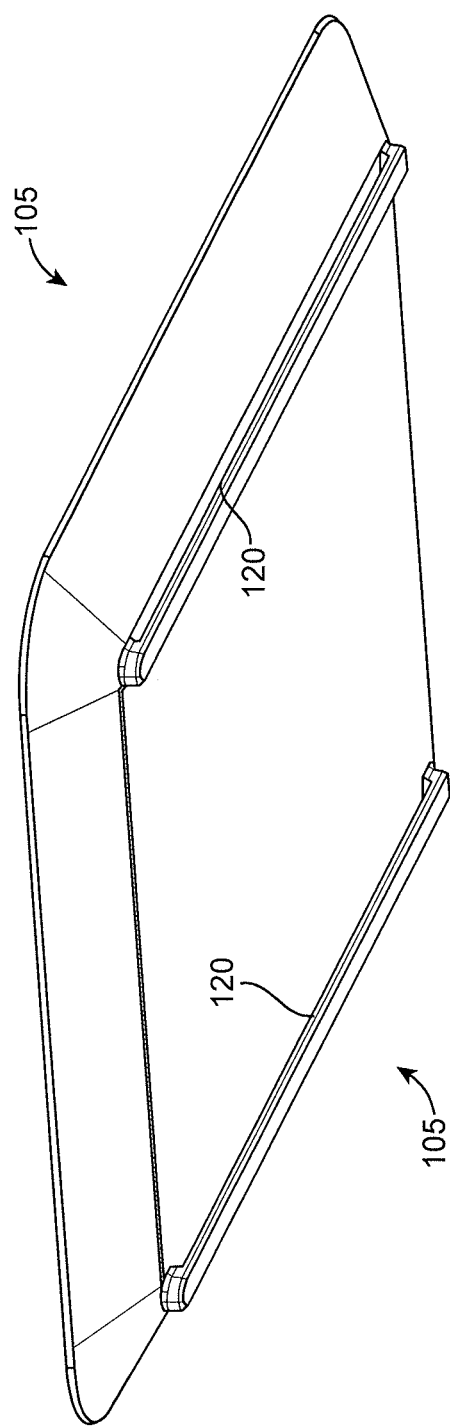
FIG. 3 shows a bottom view of the surgical tray of FIG. 2.

In another embodiment, shown in FIG. 3, the slots are formed by one or more protrusions on the lower surface of the tray 105. The protrusions contain the slots and are sized to receive the drape therethrough. Thus, when the drape is positioned through the slots, the drape is positioned adjacent the bottom surface of the tray 105.

Figure 4:
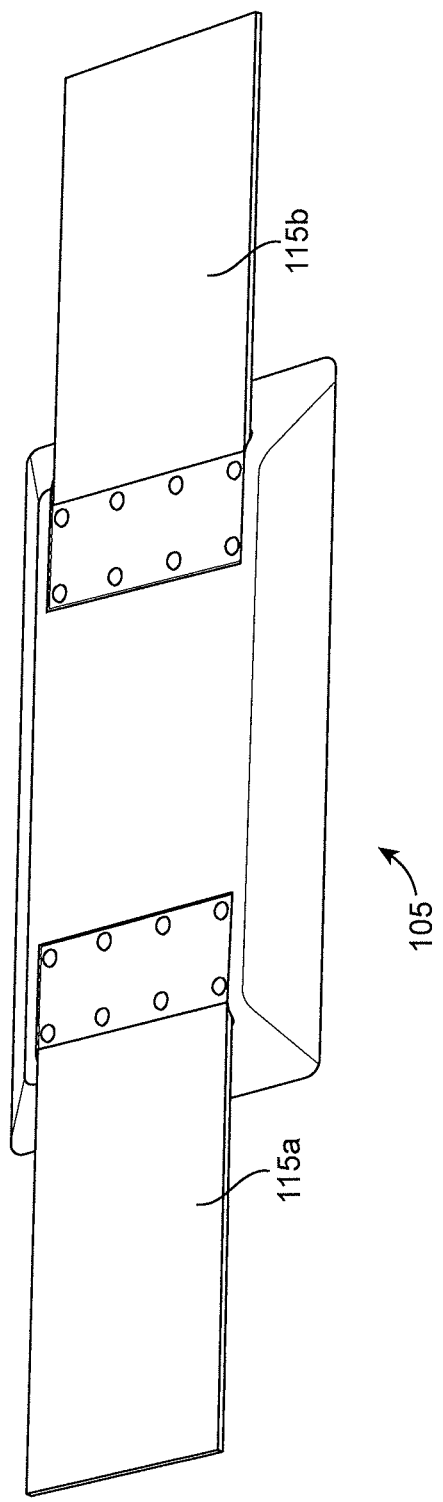
FIG. 4 shows a bottom view of yet another embodiment of a surgical tray.

FIG. 4 shows another embodiment of the tray 105 wherein the drape 115 is formed of two portions including a first portion 115a attached to one side of the tray 105 and a second portion 115b attached to the opposite side of the tray. Any attachment means, including adhesive, screws, rivets, bolts, etc., may be used to attach the first and second portions to the tray.

In an embodiment the on-patient surgical tray rests on the patient and includes the tray and a drape system, which may be placed on top of the patient and the patient's surgical drapes. Surgical clamps, clips or other attachment mechanisms may be used to couple the tray to the patient. In an embodiment the on-patient surgical tray rests on the patient and on the patient's surgical drapes.

In an embodiment, the surface of the tray 105 has seat, a cup, etc., or smaller basin molded into the tray to allow for resting of surgical or procedural instruments, such as, for example, an electrocautery pencil or a suction wand. The cup or basin can have several designed edges and size varying slits or curved edges to capture and secure the instruments. The cup or basin can also have loops or rings or holes molded into the side of the cup to secure instruments.

The tray 105 can include any of a variety of mechanisms or means for attaching items to the tray. For example, the tray 105 may include loops, rings, slits, clips, holes, or any other structure. The structure may be attached to or molded into the sides of the tray to secure instruments and allow them to dangle from the tray.

The tray may be manufactured of any of a variety of materials, including metal, plastic, wood, etc.

The tray 105 may vary in size and shape. In an exemplary embodiment the on-patient surgical tray is a plastic tray, measuring 8.5 inches long and 11 inches wide, with 30 degree from base angled elevated textured walls although these dimensions are for example only. The tray includes a pair of openings along the base to allow the tray's single elongated tray drape to pass through the two sides slit openings of the tray and serve as a contiguous single sheet forming the tray drapes and the tray base surface. The tray drapes may be attached to the patient's surgical or procedural drapes by either an external set of clamps or clips or a set of clamps or clips integrated into the ends of the drapes or any other means including adhesive. As the patient's position is changed the tray, because the tray drape is inserted through the two openings along the base, easily slides along the single drape-base to remain level and provide a safe plane and zone to pass or rest instruments without having to reattach or resecure the tray drapes to the patient's surgical procedural drapes.

The on-patient surgical tray 105 may be positioned to rest on the patient and their surgical drapes and consists of a varying sized square or rectangular tray made of made of plastic, rubber, or metal or combination thereof and tray drapes either attached to the outer sides of the tray or a single varying sized drape inserted and passed through the optional two side openings of the tray to serve as a contiguous single sheet to form the tray drapes and the tray base surface and is made of either paper, textile, plastic, or rubber or combination thereof, and the tray drape is attached to the patient's surgical or procedural drapes by either an external set of clamps or clips or a set of clamps or clips integrated into the ends of the surgical tray drapes. In an embodiment the on-patient surgical tray drapes are attached to the side of the surgical tray and the drapes have attached or molded to them at various locations loops, rings, slits or clips made of plastic, rubber or metal or textile or tape or combination thereof for the purpose of securing, holding and dangling surgical instruments The novel on-patient surgical procedural instrument tray is uniquely attached to the patient or their surgical or procedural drapes allowing the physician or surgeon to maintain a better view of patient while receiving and passing procedural or surgical instruments, eliminates the requirement for foot space found in the current state of the art surgical or bedside or table side stand-alone trays, and is easily manipulated to maintain the procedural or surgical plane base surface when moving the patient's position is required.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. An on-patient surgical instrument tray to support one or more instruments, the on-patient surgical instrument tray comprising:
a generally flat top surface to support the one or more instruments;
a sloped periphery that defines a rectangle that measures at least 8.5 inches long and 11 inches wide, and that slopes up from the generally flat top surface to retain the one or more instruments supported by the generally flat top surface;
a pair of slots formed in the surgical instrument tray proximate the sloped periphery on and between opposing sides of the length of the rectangle;
a drape slideably positioned through the pair of slots and on top of the generally flat top surface of the surgical instrument tray to substantially cover the entire surface of the generally flat top surface, the drape having a length and a width to form a tray base surface on top of the generally flat top surface and opposing tray drapes on opposite sides of the surgical instrument tray when the drape is slideably positioned through the one or more slots;
a set of clamps integrated with the drape for attaching the drape to the patient when the surgical instrument tray is on-patient; and
wherein the on-patient surgical instrument tray is configured for placement atop the torso of the patient.

2. The surgical procedural instrument tray as in claim 1, wherein the drape is formed of a fabric or textile.

3. The surgical procedural instrument tray as in claim 1, further comprising an attachment mechanism configured to attach at least one of the opposing tray drapes to a patient.

4. The surgical procedural instrument tray as in claim 3, wherein the attachment mechanism is at least one of a surgical clamp and a surgical clip.

5. The surgical procedural instrument tray as in claim 1, where the one or more slots each have a width that is-equal to the width of the drape.

6. The surgical procedural instrument tray as in claim 1, wherein the one or more slots each have a width that is equal to a width of the generally flat top surface.

7. An apparatus for placement on a patient to support one or more instruments for a surgical procedure in which the patient is at least partially covered by a surgical drape, the apparatus comprising:
a tray configured for placement on the patient for the surgical procedure, the tray having a top surface to support the one or more instruments;
a sloped periphery that defines a rectangle that measures at least 8.5 inches long and 11 inches wide, and that slopes up from the top surface of the tray to form a wall at the sloped periphery of the tray to retain the one or more instruments supported by the top surface of the tray;
a pair of slots formed in the tray proximate the sloped periphery on and between opposing sides of the length of the rectangle;
a tray drape slideably positioned through the pair of slots and on top of the top surface of tray, the tray drape having a length and a width to form a tray base surface on top of the top surface of the tray and opposing end drapes on opposite sides of the tray when the tray drape is slideably positioned through the one or more slots;
a set of clips integrated with each of the opposing end drapes of the tray drape for attaching the tray drape to the surgical drape of the patient during the surgical procedure; and
wherein the tray is configured for placement atop the torso of the patient.

8. The apparatus in accordance with claim 7, wherein the top surface of the tray is generally flat.

9. The apparatus in accordance with claim 7, wherein the top surface of the tray is contoured.

* * * * *